(12) United States Patent
Lambiase

(10) Patent No.: US 9,468,665 B1
(45) Date of Patent: Oct. 18, 2016

(54) METHOD OF TREATING INTRAOCCULAR TISSUE PATHOLOGIES WITH NERVE GROWTH FACTOR

(75) Inventor: Alessandro Lambiase, Rome (IT)

(73) Assignee: Dompé Farmaceutici S.p.A., Milan (IT)

( * ) Notice: Subject to any disclaimer, the term of this patent is extended or adjusted under 35 U.S.C. 154(b) by 0 days.

(21) Appl. No.: 09/890,088

(22) PCT Filed: Jan. 21, 2000

(86) PCT No.: PCT/IT00/00016
§ 371 (c)(1),
(2), (4) Date: Jul. 26, 2001

(87) PCT Pub. No.: WO00/44396
PCT Pub. Date: Aug. 3, 2000

(30) Foreign Application Priority Data

Jan. 29, 1999 (IT) .................................. RM99A0069

(51) Int. Cl.
*A61K 38/18* (2006.01)

(52) U.S. Cl.
CPC .................................... *A61K 38/18* (2013.01)

(58) Field of Classification Search
CPC .................................................... A61K 38/18
USPC ....... 424/422, 426, 423, 443, 445, 484, 486, 424/427, 434; 514/2
See application file for complete search history.

(56) References Cited

U.S. PATENT DOCUMENTS

| | | | |
|---|---|---|---|
| 4,959,319 A | | 9/1990 | Skelnik et al. |
| 4,973,466 A | * | 11/1990 | Reich .............................. 424/426 |
| 5,641,479 A | | 6/1997 | Linares et al. |
| 5,641,749 A | * | 6/1997 | Yan et al. ........................ 514/12 |
| 5,641,750 A | * | 6/1997 | Louis .............................. 514/12 |
| 5,736,516 A | * | 4/1998 | Louis .............................. 514/12 |
| 5,767,079 A | * | 6/1998 | Glaser et al. ................... 514/12 |
| 6,056,950 A | | 5/2000 | Saettone et al. |
| 6,063,757 A | * | 5/2000 | Urso .................................. 514/2 |
| 6,261,545 B1 | | 7/2001 | Okamoto |
| 6,436,427 B1 | * | 8/2002 | Hammang et al. ............ 424/427 |
| 2002/0009498 A1 | | 1/2002 | Clifton et al. |
| 2003/0181354 A1 | | 9/2003 | Abdulrazik |

FOREIGN PATENT DOCUMENTS

| | | | |
|---|---|---|---|
| DE | 3827477 A1 | 2/1990 | |
| EP | 0312208 | * 9/1988 | ............. A61K 37/02 |
| EP | 0 312 208 A | 4/1989 | |
| EP | 0312208 A1 | * 4/1989 | |
| EP | 312208 A1 | * 4/1989 | |
| EP | 0572364 A2 | 12/1993 | |
| JP | 2002-531490 A | 9/2002 | |
| WO | WO 92/15614 A1 | 9/1992 | |
| WO | WO 98/10785 A | 3/1998 | |
| WO | WO 98/48002 | * 10/1998 | |
| WO | WO 98/48002 A | 10/1998 | |
| WO | WO 9848002 A1 | * 10/1998 | |
| WO | WO 90/12590 A | 1/1999 | |
| WO | WO 00/07613 A1 | 2/2000 | |
| WO | WO 00/33814 A2 | 6/2000 | |
| WO | WO 00/44396 A1 | 8/2000 | |

OTHER PUBLICATIONS

Steadman's Medical Dictionary (Lippincott Williams & Wilkins, 2000)—definitions of "endothelium," "cornea," and "sclera".*
The World's Best Anatomical Charts (Anatomical Chart Company, Skokie, IL, 2000) (Sagittal View of the Eye) (pp. 16 and 17) (4 pages total).*
Machine language translation of Okamoto, JP 10-218787 (Aug. 18, 1998).*
Levi-Montalcini et al., (Proc Natl Acad Sci USA. Oct. 1985;82(20):7111-5).*
Siliprandi et al., (Invest Ophthalmol Vis Sci. Nov. 1993;34(12):3232-45).*
Steadman's Medical Dictionary definition of "Ganglion Cells of Retina" (Lippincott Williams & Wilkins. 2001).*
English Translation of JPH10218787A. Morningside Translations. Certificate dated May 25, 2016.*
Patent Abstracts of Japan, vol. 1998, No. 13 (Nov. 30, 1998) and JP 10 218787 A (Okamoto Akio), Aug. 18, 1998 Abstract.
Lambiase et al., "Nerve Growth Factor Delays Retinal Degeneration In C3H Mice," Chemical Abstracts & Indexes, US, American Chemical Society, Columbus, vol. 125, No. 19, (Nov. 4, 1996) (XP-002058562).
RAPP, "Retinal Phototoxicity", Handbook of Neurotoxicology (Editors: Chang, et al.), Marcel Dekker, Inc., Chapter 32, 1995, pp. 963-1003.
US Office Action, dated Feb. 5, 2013, for U.S. Appl. No. 13/372,742.
English translation of WO-00/07613-A1, dated Feb. 17, 2000.
U.S. Office Action, dated Oct. 2, 2012, for U.S. Appl. No. 12/064,172.
EPO International Search Report, Appl. No. PCT/IT2006/000620, Feb. 9, 2007.
Jackowski, A., "Neural injury repair: hope for the future as barriers to effective CNS regeneration become clearer," British Journal of Neurosurgery, 1995, vol. 9, pp. 303-317.
Lambiase, A. et al, "Increased Plasma Levels of Nerve Growth Factor in Vernal Keratoconjunctivitis and Relationship to Conjunctival Mast Cells," Invest Ophthalmol Vis Sci., Chemical Abstracts, Sep. 1995, vol. 136, No. 10, pp. 2127-2132.

(Continued)

*Primary Examiner* — Cherie M Stanfield
(74) *Attorney, Agent, or Firm* — Fish & Richardson P.C.

(57) ABSTRACT

Nerve Growth Factor (NGF), in the form of a preparation to be administered over ocular surface, is suggested as being suitable for therapy and/or prophylaxis of intraocular tissue pathologies, with particular reference to sclera, ciliary body, crystalline lens, retina, optic nerve, vitreous body and choroidea affections. When administered in the form of external ophthalmic preparation, for example as collyrium or ointment, NGF is capable to go through ocular tissues and it has been found out that it shows a therapeutic activity not only against retina and optic nerve pathologies but also against affections involving the above reported internal structures of the eye.

14 Claims, No Drawings

(56) References Cited

OTHER PUBLICATIONS

Lambiase, A. et al, "Nerve growth factor delays retinal degeneration in C3H mice," Graefe's Arch Clin Exp Ophthalmol, Chemical Abstracts, Nov. 4, 1996, vol. 25, No. 19.
Response to Mar. 12, 2004 Office Action, which issued in European Application No. 0090133.9-2107.
USPTO Office Action, U.S. Appl. No. 12/064,172, Jun. 13, 2011.
Office Action for U.S. Appl. No. 13/372,742, dated Jun. 18, 2013.
U.S. Office Action, dated Jul. 30, 2013, for U.S. Appl. No. 13/372,742.
Advisory Action issued Jan. 18, 2013, in U.S. Appl. No. 12/064,172.
Advisory Action issued Oct. 15, 2013, in U.S. Appl. No. 13/372,742.
Office Action issued Oct. 7, 2013, in U.S. Appl. No. 12/064,172.
de Castro et al., "Corneal innervation and sensitivity to noxious stimuli in trkA knockout mice," European Journal of Neuroscience (1998), vol. 10, pp. 146-152.
English translation of Figure 1 of JP 10-21878 A (Aug. 18, 1998).
Hamel, C., "Retinitis pigmentosa," Orphanet Journal of Rare Diseases (2006), vol. 1, No. 40, pp. 1-12.
Hartong et al., "Retinitis pigmentosa," Lancet (2006), vol. 368, pp. 1795-1809.
La Vail, M. M., "Photoreceptor characteristics in congenic strains of RCS rats," Invest. Ophthalmol. Vis. Sci., Reports (May 1981), pp. 671-675.
Lambiase, A. and L. Aloe, "Nerve growth factor delays retinal degeneration in C3H mice," Graefe's Arch. Clin. Exp. Ophthalmol. (1996), vol. 234, pp. S 96-S 100.
Llamosas et al., "Neurotrophin receptors expression in the developing mouse retina: an immunohistochemical study," Anat. Embryol. (1997), vol. 195, pp. 337-344.
Office Action issued Apr. 11, 2014, in U.S. Appl. No. 13/372,742.
Office Action issued Dec. 1, 2011, in U.S. Appl. No. 12/064,172.
Smith et al., "AAV-Mediated Gene Transfer Slows Photoreceptor Loss in the RCS Rat Model of Retinitis Pigmentosa," Molecular Therapy (Aug. 2003), vol. 8, No. 2, pp. 188-195.
Translation of Official Action issued Dec. 27, 2011, in JP Application No. 2008-526617.
Wahlestedt et al., "Neurogenic Mechanisms in Control of the Rabbit Iris Sphincter Muscle," European Journal of Pharmacology (1985), vol. 117, pp. 303-309.
Jackowski, British Journal of Neurosurgery 9:303-317 (1995).

* cited by examiner

METHOD OF TREATING INTRAOCCULAR TISSUE PATHOLOGIES WITH NERVE GROWTH FACTOR

The present invention relates to the use of nerve growth factor for the therapy of intraocular tissue pathologies. More particularly, the invention relates to the use of the neurotrophin, named nerve growth factor (NGF), for the therapeutic treatment of the eye internal structures, as sclera, choroidea, ciliary bodies, crystalline lens, vitreous body, retina and optic nerve, by a topical administration over the ocular surface, i.e. as collyrium or ophthalmic ointment.

The nerve growth factor (NGF) is the chief molecule of a complex neurotrophin family, and is well known for its trophic, tropic and differentiating activity on cholinergic neurons of the central nervous system and on the sympathetic peripheral system. NGF is produced by various mammalian tissues, included humans, and is released in the circulatory flow in greater amounts during the growth and differentiation of the nervous system. Biological, biochemical and molecular studies carried out on in vitro cellular systems have pointed out high sequence homology between murine and human NGF. Furthermore, in humans and other mammalians NGF is normally contained both in the cerebrospinalis liquor and blood flow at concentrations of about 10-15 pg/ml. The value increases during some inflammatory pathologies (autoimmune and allergic diseases, etc.), whereas decreases in others (diabetes).

NGF has been discovered by Prof. Rita Levi-Montalcini, at the Zoology Institute of St. Louis Washington University (Levi-Montalcini R., Harvey Lect., 60:217, 1966), and its discovery represented a remarkable step for studying mechanisms of growth and differentiation of nerve cell, being able to affect the development and preservation of the biological functions and the regeneration of the neurons. In 1986 the Nobel Prize for Medicine and Physiology was assigned to Prof. R. Levi-Montalcini for the discovery and characterization of biological function both in peripheral and central nervous system of this molecule.

Various experimental studies both in vitro and in vivo have demonstrated the NGF physiopathological importance to prevent neuron damages of surgical, chemical, mechanical and ischemic origin, allowing it to be used as ideal compound for the therapy of various pathologies affecting both the peripheral and central nervous systems (Hefti F., J. Neurobiol., 25:1418, 1994; J. Fricker, Lancet, 349:480, 1997). In fact some years ago clinical tests have been carried out on subjects affected by Parkinson's Disease and Alzheimer's Disease by intracerebral administration of murine NGF (see, for example, Olson L. et al., J. Neural Trans.: Parkinson's Disease and Dementia Section, 4:79, 1992). Results of these experiments confirmed observations obtained from animal models and pointed out the absence of possible side effects following the administration of murine NGF. This behaviour has been confirmed more recently for recombinant human NGF (Petty B. G. et al., Annals of Neurobiolgy, 36:244-246, 1994).

Studies referring to the characterization of biological, biochemical, molecular, pre-clinical and clinical effects almost exclusively have been carried out using NGF isolated from submandibular glands of adult rodents; therefore available data concern mostly murine NGF. Biochemical properties of the latter, particularly, have been described in a study published in 1968 (Levi-Montalcini R. and Angeletti P. U., Physiological Reviews, 48:534, 1968).

NGF contained in murine salivary glands is a 140 kdalton molecular complex, the sedimentation coefficient thereof being 7S, and it is constituted by three sub-units, $\alpha$, $\beta$ and $\gamma$, the second of which represents the actual active form. The latter, called $\beta$NGF, whose sedimentation coefficient is 2.5S, is usually extracted and purified according to three not very different techniques (Bocchini V., Angeletti P. U., Biochemistry, 64; 787-793, 1969; Varon S. et al., Methods in Neurochemistry, 203-229, 1972; Mobley W. C. et al., Molecular Brain Research, 387:53-62, 1986).

The so obtained $\beta$NGF is a dimer of ~13.000 dalton, constituted by two identical chains of 118 amino acids. Each chain is stabilised by three disulphide bridges, while not covalent bonds assure the stabilisation of the dimeric structure. The molecule is very stable and is soluble in almost all solvents, both aqueous and oily, maintaining unchanged its biochemical characteristics and biological activity. Further details about the structure, physical and biochemical properties of the molecule are reported in Green, L. A. and Shorter, E. M., Ann. Rev. Neurosci., 3:353, 1980.

Recently the structure of $\beta$NGF has been further disclosed by means of crystallographic analysis. The analysis pointed out the presence of three anti-parallel filament pairs, having a $\beta$-type secondary structure, forming a flat surface along which the two chains join together resulting in the active dimer. On these $\beta$NGF chains the presence of four "loop" regions has been showed, wherein are included many variable amino acids probably responsible for receptor recognition specificity.

The NGF biological effect is mediated by two receptors present on the corresponding target cells. The existence of various antibodies that selectively inhibit the NGF biological effect has allowed an accurate characterization and modulation of the activity thereof, both in cellular systems and in vivo.

More recently human NGF has been synthesized using genetic engineering techniques (Iwane et al., Biochem. Biophys. Res. Commun., 171:116, 1990) and small amounts of human NGF are commercially available too. However the author of the invention discovered that the biological activity of human NGF is very low when compared to murine NGF. Furthermore it is to be pointed out that almost all of data available concerning human NGF, both in vivo and in vitro, have been obtained using murine NGF and undesirable side-effects resulting from murine origin of molecule have never recognised.

Studies carried out since 90's using animal models suggested a possible NGF involvement in ocular pathologies. Apart of some patent publications wherein NGF is not the object of actual experimental results, but is only mentioned together with other known growth factors (on the basis of the unverified assumption that it belongs to an homogeneous class of molecules having equivalent characteristics and biological activities), and apart of the PCT patent application No. WO98/48002, under the Applicant's name, wherein the use of NGF in the therapy for cornea and conjunctiva pathologies is suggested (discussed in detail below), the scientific reports published in the ophthalmic field exclusively refer to the use of NGF for retina and optic nerve affections.

Particularly it has been reported that the intraocular NGF administration to animal models is effective for enhancing the survival of retinal ganglion cells following acute retina ischemia (Siliprandi R. et al., Inv. Ophthalmol. Vis. Sci., 34:3232, 1993) and optic nerve trans-cutting (Carmignoto G. et al., J. Neurosci., 9:1263, 1989). More recently the NGF administration by intra-vitreous or also retro-bulbar injections proved to be effective for the mouse retinal degeneration model, which is similar to human pigmentary retinopathy (Lambiase A. and Aloe L., Graefe's Arch. Clin. Exp. Ophthalmol., 234:S96-S100, 1996), and for the rabbit retinal damage model resulting from ocular hypertension (Lambiase A. et al., Graefe's Arch. Clin. Exp. Ophthalmol., 235: 780-785, 1997).

Such experimental studies showed that the local NGF administration is effective for preventing or at least delaying the death of retinal ganglion cells and photoreceptors resulting from above said pathologies. In addition side effects during animal treatments have not been reported. However it is to be pointed out that in all the publications above reported, NGF is administered to the ocular tissue by intravitreous or also retro-bulbar injection.

The PCT patent application No. WO98/48002 up to now is the only document wherein the use of NGF as external ophthalmic application, for example in the form of collyrium or ointment, is described. Experimental work therein reported proves that topically administered NGF is suitable for a successful treatment of ocular surface pathologies (cornea and conjunctiva) both of acquired and congenital type and, particularly, of various dystrophic or neurodystrophic pathologies for which therapeutic treatments did not exist previously. The discovery of the presence of NGF and of its high affinity receptor (TrkA, tyrosinkinase A), by immunohystochemical techniques, was the condition for such innovative result. Evidently the expression of the NGF high affinity receptor is an essential prerequisite for NGF to exert its therapeutic activity.

During the studies of the instant invention, always by both immunohystochemical and immunofluorescence techniques (Lambiase et al., J. Allergy Clin. Immunol., 100:408-414, 1997) and biomolecular techniques as well for the in situ identification of the NGF mRNA (Micera A. et al., Archives Italiennes de Biologie, 133:131-142, 1995), it has been pointed out that any cell contained in sclera, crystalline anterior capsule, ciliary body epithelium, optic nerve fibers, retinal ganglion cells, retinal pigmented epithelium cells and some choroidea cells not only express the receptor having high affinity for NGF but are also able to produce this neurotrophin (not yet published data). The experimental data result in various implications. On the one hand NGF, released from cells of various ocular tissues, should exhibit a trophic and physiopathological activity in all the ocular regenerative mechanisms; on the other hand various pathologies of trophic, degenerative or immune type should recognise the failed release of NGF as fundamental etiologic chance.

Furthermore, because the effects observed after the administration of exogenous NGF are present at almost physiological concentrations (in the order of about a few micrograms), it is conceivable that in some ocular affections the reduction of local NGF levels under the threshold value suitable to assure the tissue integrity can be a possible physiopathogenetic mechanism. Such a pathogenetic hypothesis is confirmed by the effects derived from NGF deprivation, both in vivo and in vitro, that induces the death of various cell population and the exacerbation of tissue damages of chemical, physical, infective or degenerative type (Aloe L., Int. J. Devl. Neuroscience, volume 5(4), 1987; Lambiase A. and Aloe L., above reported; Lambiase et al., Graefe's Arch. Clin. Exp. Ophthalmol., 1997, above reported).

Although the above results allow to hypothesise a therapeutic activity of NGF also for ocular structures and tissues different than those already reported in literature, and specifically for sclera, ciliary body, crystalline, vitreous body and choroidea, there is the problem for an easy administration of the active principle to involved tissues. Contrary to the case considered in the PCT patent application No. WO98/48002, referring to cornea and conjunctiva pathologies, herein tissues within bulb of eye are involved.

The possibility of an external topical administration for an ophthalmic therapeutic agent, i.e. in the form of collyrium or ointment, represents a remarkable benefit in comparison with the administration through parenteral topical, retrobulbar or intravitreous injection routes. In fact the use of these latter techniques involves the risk for various complications, reported in literature, as the ocular bulb perforation, infections, haemorrhages and lesions of anatomical structures during injection. Such complications can occur also more frequently during the treatment of chronic pathologies, and can lead to the unfeasibility of the therapy due to the inversion of risk/benefit ratio.

The author has surprisingly found that by administration of NGF in the form of collyrium, an increase of such a neurotrophin levels in all ocular tissues, including those into the ocular bulb, is obtained. As it will be illustrated in detail in the following experimental report, the passage of NGF from the ocular surface, where it is administered, to internal ocular tissues, has been showed using both an autoradiographic method (Levi-Montalcini, R and Aloe L., Proc. Natl. Sci. USA 82:7111-7115, 1985), and an immunoenzymatic assay (Bracci-Laudiero, L. et al., Neurosci. Lett., 147:9-12, 1992). The application of the latter method on rabbits treated by conjunctival instillation of a NGF-containing saline solution has caused, one hour after the administration, an increase of NGF concentration in all the examined ocular tissues. The NGF level is reduced to initial levels after 6-8 hours. This effect allows NGF to express its therapeutic activity also in not directly involved tissues by a superficial administration. This aspect is innovative not only with reference to the ophthalmic pathologies for which till now the NGF therapeutic activity was not even conceivable, but also for retina and optic nerve pathologies, wherein the NGF possible activity has been already reported, but it was not yet available a drug administration in a ready and safe way without risks and drawbacks for the patient.

Therefore it is a specific object of the present invention, according to a first aspect thereof, the use of nerve growth factor (NGF) for the production of an ophthalmic preparation to be administered over the ocular surface for the therapy and/or prophylaxis of intraocular tissue pathologies. Specifically said NGF containing ophthalmic preparation is in the form of solution or suspension (collyrium), ointment, gel or liniment together with a pharmaceutically acceptable, eye tolerated and compatible with active principle ophthalmic carrier. It is also possible to conceive particular routes for ophthalmic administration for delayed release, as ocular erodible inserts, or polymeric membrane "reservoir" systems to be located in the conjunctiva sac. Alternatively NGF, or a preparation containing it, can be added to a local bandage together with a therapeutic contact lens.

As already pointed out said ophthalmic preparation is suitable for the therapy and/or prophylaxis of sclera, ciliary body, crystalline lens, retina, optic nerve, vitreous body and choroidea pathologies, said affections having trophic, post-traumatic, infective, post-surgical, autoimmune, dystrophic, degenerative, post-inflammatory and laser treatment origin. As it will been demonstrated by experimental data below reported, the NGF external topical administration proved, among other things, to be able to repair sclera lesions of traumatic or immune origin, to cause an increase of aqueous humour production, restoring the intraocular pressure in pathologies characterised by hypotonia and resulting in bulbar phthisis and to prevent and delay the formation and progression of crystalline lens opacity (cataract). As to retinal pathologies, the NGF administration by application over ocular surface induces an increase of nervous fiber thickness, a survival of retina ganglion cells, photoreceptors, pigmented epithelium during degenerative, ischemic, traumatic pathologies and when damages from ocular hypertonia are present. As to optic nerve the effects obtained are an improvement of visual evoked potentials (PEV), visual field and survival of nervous fibers when traumatic, ischemic, pressor and degenerative pathologies occur. Finally as to choroidea the NGF administration by external ophthalmic application causes a reduction of choroidea inflammatory processes and reduces the number of mobile vitreous bodies. It is to be pointed out that many of these disorders are hardly therapeutically treated, or they lack of an effective treatment.

The possibility that nerve growth factor could exhibit a biological activity on internal tissues of ocular bulb following an external local administration was hardly predictable mainly considering that, as before pointed out, NGF is a quite big molecule (26.800 dalton) with a complex structure. In order that a molecule can exert its activity on deep ocular tissues, it is necessary that, once it has been instilled over the eye surface, the molecule pass through the lacrimal layer, cornea, aqueous humour and vitreous body so to be distributed within all the tissues. According to the current practice such molecules (particularly antibiotics or cortisone molecules) which are able to reach the crystalline lens, vitreous body and retina at therapeutically effective concentrations are not available. For the above reasons in all the known studies on the utilisation of NGF for ocular pathologies, only the intraocular administration route was used.

In effect NGF, although has a complex structure and high molecular weight, includes both hydrophilic and hydrophobic groups which allow it to pass through the homologous (lipid and hydrophilic) anatomical barriers. Furthermore it is a basic characteristic of NGF that once it has reached target organs, also at very low but yet biologically active concentrations, it is able to stimulate tissue to produce endogenously the NGF. The presence of an endogenous produced NGF is clearly suggested by experimental results concerning the NGF passage through tissues. These results furthermore show that a concentration gradient is not maintained from the external surface to deeper eye tissues, as it would be conceivable in the presence of a simple diffusion mechanism through the tissues.

In order to carry out the preparation according to the present invention suitable procedures for the NGF extraction and purification are reported in the previously cited references. The technique according to Bocchini and Angeletti, herein briefly reported, has been used for the experiments of the present invention. Submandibular glands of adult male mice are collected in a sterile way and tissues thereof are homogenised, centrifuged and dialysed; then the obtained suspension is passed through subsequent cellulose columns, whereon NGF is adsorbed. Following NGF is eluted with a buffer containing 0.4 M sodium chloride. The obtained samples are analysed spectrophotometrically at a 289 nm wavelength to identify the NGF containing fractions. These fractions are dialysed and the NGF is lyophilised in a sterile way and stored at −20° C. in freezer.

A medicament according to the invention suitable for administration onto the ocular surface preferably contains, alone or in association with one or more other active principles, from 1 to 1000 µg/ml of NGF. In the case the product is in the form of an aqueous solution (collyrium), the concentration of NGF is preferably between 10 and 500 µg/ml. A specific formulation suitable in the form of collyrium contains, for example, 200 µg/ml of NGF in physiological solution containing 0.9% of sodium chloride, or in balanced saline solution ($BSS^R$); in both circumstances the solution is isotonic with lacrima and therefore well tolerable by the eye. However it is also possible the use of hypotonic solutions.

The NGF contained in the saline solution can be present alone or in association with other biologically active molecules, and/or conjugated with carrier molecules (as, for example, transferrin). In order to further enhance its passage through ocular surface, other excipients selected from those conventionally used according to pharmaceutical techniques, for example to buffer the solutions or suspensions, to stabilise the active principle and make the preparation well tolerable can be added. Specifically buffers should keep pH between 4 and 8. For example the above reported sodium chloride solution can be buffered using any of the buffers well known in the pharmaceutically field as suitable for ophthalmic use, among which phosphate or trizma (tri-hydroxymethyl-aminomethane) buffers, so to have a physiological pH, i.e. 7.0-7.4, maintaining simultaneously a physiological osmolarity (295-305 mOsm/l).

The tolerability can be further enhanced using excipients like polysorbate 80 (or Tween 80), dextran, polyethylene glycol (for example PEG 400) and like. The formulation can contain also viscosity-enhancing agents like hyaluronic acid, methylcellulose, polyvinylalcohol, polyvinylpyrrolidone and others, in order to enhance the ocular bioavailability, stability and tolerability of the active principle. The ocular bioavailability of NGF can be further enhanced by using compounds that ameliorate the corneal permeation of the drug as, for example, dimethylsulfoxide, taurocholates, membrane phospholipids and various surfactant agents suitable for ophthalmic use. In addition to prevent contamination, a preservative agent having antimicrobial activity can be added to the formulation.

Agents like carboxymethylcellulose or like can be added to products to be administered in form of suspension. If it is desired to use the formulation in the form of ointment, gel or ophthalmic liniment, the NGF carrier could be polyethyleneglycol, polyacrylate, polyethyleneoxide, fatty acid and alcohol or lanolin, paraffin and similar products.

As already pointed out the therapeutic activity of nerve growth factor against ocular tissues other than superficial (cornea and conjunctiva), retina, optic nerve has been not previously disclosed neither when it is administrated by intraocular injection nor by formulations in the form of collyrium or ointment. Therefore it is a further object of the invention the use of nerve growth factor (NGF) to produce an ophthalmic preparation for the therapy and/or prophylaxis of intraocular tissues pathologies, except retina and optic nerve pathologies, whatever the administration route is.

Again the concentration of NGF in the preparation is preferably between 1 and 1000 µg/ml of NGF and all the conventional formulation procedures well known in the field can be used and particularly those previously reported with reference to the ophthalmic formulations for external administration.

Some experimental results, obtained within the scope of the present invention, including clinical data concerning therapeutic applications on humans, are below reported merely for exemplary purposes.

Studies on the Passage of NGF Through Ocular Tissues

In a first set of tests to study the passage of NGF intraocularly from external surface over which it was administered, the above mentioned autoradiographic method has been used for a group of six rabbits. Each of the animals was administered with one collyrium drop (50 µl) containing 10 µg of $I^{125}$ labeled NGF (concentration: 200 µg/ml) by instillation in the conjunctiva fornix.

Murine NGF purified according to the previously described method and subsequently conjugated to Na—$I^{125}$ (Amersham Italia, IMS30, 1 mCi) according to chloramine T method (Lapack P A. Exp. Neurol. 124:1620, 1993) has been used. The amount of labeled NGF has been determined by chromatography using a Sephadex G-25 column. The amount of the $I^{125}$ labeled product collectible by precipitation was between 90% and 95%, showing that the most of the radioactive product was bonded to NGF. The specific activity of NGF-$I^{125}$ was between 1 and 1.5 Ci/µmol.

Two hours following the administration of the labeled NGF the animals were sacrificed and eyes enucleated and fixed in 4% paraformaldehyde over 48 hours. Then samples, after incubation in 30% sucrose over 24 hours, were cut with a cryostat to 15 µm thick sections. Sections were mounted on histology gelatinous slides, immersed in photographic emulsion (Ilford K2) and incubated over 4 weeks at 4° C. Sections were successively dehydrated using ethanol, mounted on DPX after treatment with xylene and examined with Zeiss optical microscope.

This experiment showed that labeled NGF, after its administration over ocular surface, was able to penetrate into eye and bond with cells of various tissues contained in the posterior segment and crystalline lens inducing the expression of the specific receptor.

In a second set of tests, using above described immunoenzymatic method, the quantitative levels of NGF in various ocular tissues after the administration by instillation of a drop of murine NGF in the conjunctiva fornix were determined. In all 24 rabbits were used, six thereof were sacrificed immediately to determine initial values of NGF concentration in various ocular tissues. Remaining animals were sacrificed after 1 (6 rabbits), 2 (6 rabbits) and 8 hours (6 rabbits) following the administration of the collyrium.

In all the cases the eyes were enucleated and the different tissues (cornea, sclera, aqueous, iris, crystalline lens, retina, choroidea, optic nerve) were sectioned. The tissues were weighted, sonicated (using Braun B Sonicator) in a buffered protein matrix containing protease inhibitors (extraction buffer). Thus obtained homogenate was centrifuged (×10000 rpm for 20 minutes) and surnatant was used to determine the levels on NGF by immunoenzymatic method (ELISA). This technique is extremely sensitive and NGF specific and it is able to detect concentrations up to 5 pg/ml. Goat anti-NGF polyclonal antibody, diluted in 0.05 M carbonate buffer, pH 9.6, was used as first antibody. As control, for the determination of unspecific signal, purified goat immunoglobulins were used.

Solutions containing primary antibody and control immunoglobulins were plated in parallel on polystyrene 96 well plates. Then the plates were incubated for 12 hours at room temperature and following the unspecific sites were blocked using a solution containing carbonate buffer plus 1% BSA. Further to plate washings with 50 mM Tris-HCl, pH 7.4, 200 mM NaCl, 0.5% gelatine, and 0.1% Triton X-100, NGF samples and standard solutions were suitably diluted with 50 mM Tris-HCl, pH 7.2, 400 mM NaCl, 4 mM EDTA, 0.2 mM PMSE, 0.2 mM benzethonium chloride, 2 mM benzimidine, 40 U/ml aprotinin, 0.05% sodium azide, 2% BSA and 0.5% gelatine. After triplicate distributions of standard solutions and samples of NGF in an amount of 50 µm/well, plates were incubated with the secondary antibody: 4 mU/well of anti-β-galactosidase (Boerhinger Mannheim, Germany) for 2 hours at 37° C. Then, after the washings, 100 µl/well of a solution containing 4 mg of β-galactosil-chlorophenol red (Boerhinger Mannheim Germany)/ml of 100 mM HEPES, 150 mM NaCl, mM $MgCl_2$, 0.1% sodium azide and 1% BSA solution were distributed.

After the incubation of the chromogen for a period of two hours at 37° C. the optical density at wavelength of 575 nm was determined using ELISA reader (Dynatech). The concentration values of NGF standards and samples were calculated after subtraction of background values due to unspecific bonds. Data reported as pg/ml or pg/g are referred to fresh weighted tissue. Results, resumed in the following Table 1, show that: after one hour form the collyrium administration in all the intraocular tissues the NGF concentration values are increased, these values are maintained high, although reduced, and after 8 hours they are again the same as the initial ones.

TABLE 1

NGF concentrations in various ocular tissues after NGF administration in the form of collyrium (NGF pg/g of tissue)

| HRS | SCLERA | CHOROIDEA | RETINA | OPTIC NERVE | CRYSTALLINE LENS | VITREOUS BODY |
|---|---|---|---|---|---|---|
| 0 | 100 ± 50 | 960 ± 400 | 83 ± 50 | 83 ± 50 | 100 ± 15 | 10 ± 4 |
| 1 | 1414 ± 30 | 2800 ± 700 | 484 ± 70 | 1195 ± 180 | 200 ± 30 | 73 ± 12 |
| 2 | 694 ± 150 | 1813 ± 900 | 322 ± 100 | 342 ± 115 | 150 ± 20 | 20 ± 5 |
| 3 | 200 ± 100 | 100 ± 500 | 150 ± 70 | 130 ± 100 | 110 ± 20 | 10 ± 5 |

Studies on the Effect of NGF Administration in the Form of Collyrium for Sclera Pathologies Presently therapeutic treatments effective to induce reparations for both traumatic and immune or infective sclera lesions are not known. In the case of autoimmune pathologies the formation of malacic sclera zones (scleromalacia) occurs which tend progressively to enlarge and become deeper with possible bulb perforation. Surgical treatment is the unique usable therapy and it includes the coating of damaged or malacic zone with a layer of human stored sclera or other biocompatible human tissues. However in the case of immune affections, recidivations of sclera pathology often occur.

In the studies in connection with the present invention the effect of external administration in the form of collyrium of murine NGF (2.5S), at a concentration of 250 µg/ml in balanced saline solution, was evaluated for 4 cases of sclera lesions, 2 of which post-traumatic and 2 scleromalacic by autoimmune diseases (reumatoid arthritis, AR and systemic lupus erythematosus, respectively). Therapeutic protocol included the daily instillation of one or two drops of preparation in the following way: during the first two days every two hours, six times a day up to the second day from the complete sclera reparation and four times a day during the following fifteen days. Therapy, once interrupted, should immediately again carried out if initial signals or symptoms of recidivations of sclera pathology are present.

All the patients within two weeks from the beginning of the treatment with NGF showed clear signals of recovery. None thereof showed occurrence of local or systemic side effects during or after the treatment. Obtained data are summarised in the following table.

TABLE 2

Effect of treatment with NGF in the form of collyrium for sclera pathologies

| Pat. No. | Pathology | Age years Sex | Occur- rence | Extension | NGF Treatment | Outcome | Follow up |
|---|---|---|---|---|---|---|---|
| 1 | perforating trauma | 35, F | 4 days | 4 mm | 21 days | recovery | 8 months |
| 2 | perforating trauma | 42, M | 5 days | 6 mm | 25 days | recovery | 6 months |
| 3 | scleromacia in AR | 55, F | 30 days | 5 mm | 20 days | recovery | 10 months |
| 4 | scleromacia in LES | 42, M | 25 days | 4 mm | 17 days | recovery | 8 months |

Studies on the Effect of NGF Administration in the Form of Collyrium for the Production of Aqueous Humour Effect of topical administration of NGF on the production of aqueous humour was determined first on a in 10 set of 6 normal pressure rabbits. Using a tomography based method including a probe in anterior chamber of eye which is able to evaluate the modifications in the production of aqueous humour, it was recognised that the administration of NGF in the form of collyrium every two hours at a concentration of 200 μg/ml, in balanced saline solution, induces a five-fold increase in the production of aqueous humour. Such an increase is maintained during all the period of treatment.

On the base of the results obtained on animal model three patients with remarkable ocular hypotonia, in two of which following surgical treatments (2 eyes) and the other by relapsing chronic uveitis. Due to very low intraocular pressure values (<4 mm Hg), rapidly medical conditions were degenerating to bulb phthysis. The therapeutic protocol included the instillation of one or two drops of NGF preparation (200 μg/ml) in balanced saline solution every two hours until a successful clinical outcome.

All the treated patients exhibited clear symptoms of recovery within two weeks from the beginning of NGF treatment, intraocular pressure values being again between 8 and 12 mm Hg within 4 weeks. None patient showed the occurrence of local or systemic side effects during the treatment or the following period. Obtained data are summarised in the following table.

TABLE 3

Effect of the administration of NGF in the form of collyrium on production of aqueous humour

| Pat. No. | Pathology | Age years Sex | Occur- rence | NGF Treatment | Outcome | Follow up |
|---|---|---|---|---|---|---|
| 1 | vitrectomy | 40, M | 30 days | 21 days | 9 mm Hg | 7 months |
| 2 | vitrectomy | 53, F | 25 days | 25 days | 10 mm Hg | 11 months |
| 3 | chronic uveitis | 45, F | 40 days | 20 days | 12 mm Hg | 10 months |

Studies on the Effect of NGF Treatment in the Form of Collyrium for the Cataract Prevention Because it has been recognised that cells of crystalline lens capsule express the receptor with high affinity for NGF and simultaneously produce this neurotrophin, it was studied whether variations of local values of NGF resulted in formation of crystalline lens opacity (cataract, a process usually related to senescence phenomena, diabetes, steroid treatment, traumas or physical stresses) and whether the topical administration of NGF could prevent the formation or progression thereof.

To demonstrate the activity of NGF firstly a model for in vitro formation of cataract was used. In the study 18 crystalline lenses from adult rats were collected and incubated in a xilose containing medium. Then 6 crystalline lenses were treated by the addition to the medium of amounts of murine NGF variable between 1 and 300 pg/ml, 6 crystalline lenses were treated by the addition of amounts of anti-NGF antibody between 500 and 1000 μg and the remaining were left untreated as control. After 48 hours from the beginning of the culture it was clear that 6 crystalline lenses treated with anti-NGF antibody exhibited almost full cataract, whereas 6 control crystalline lens exhibited cortical cataract with poor involvement of nucleus of crystalline lens. Remaining 6, treated with NGF, exhibited only rare opacity traces, the best response being obtained with NGF concentration of about 200 pg/ml in culture medium.

To confirm the in vivo NGF activity in preventing the cataract occurrence a cataractogenesis animal model involving a diet including 30% glycerol was used. All the animals (100%) subjected to this diet exhibit a cataract within 44° day. A group comprising ten animals was treated by three daily administrations of NGF in the form of collyrium at a concentration of 200 μg/ml in balanced saline solution, a second group again comprising ten animals was subjected to a treatment with anti-NGF antibodies injected in the anterior camera and the last group of animals was treated with saline solution in drops and was used as control.

All the rats of the group treated with anti-NGF antibody developed a cataract within 30° day from the beginning of the experiment; all the rats treated with saline solution developed a cataract within 45° day from the beginning of the experiment, whereas only two rats of the group treated with NGF (20%) developed a cataract within 45° day.

Studies on the Effect of NGF in the Form of Collyrium for Retina Pathologies

To evaluate the efficacy of the NGF administration on ocular surface for retina pathologies in a first step experiments disclosed in literature carried out on animal models were repeated using, in addition to intravitreous or retrobulbar administrations, the administration of NGF in the form of collyrium, every two hours, at a concentration of 250 μg/ml in saline balanced solution. In all the experiments both in retinal ischemic and ocular hypertonia damage NGF administered in the form of collyrium exhibited the same activity as when administered by other administration routes.

On the basis of the results obtained from animals a total of 7 patients were treated, three of which suffering from pigmentary retinopathy, two for senile atrophic maculopathy and one for myopic retinopathy. Therapeutic protocol included the instillation of one or two drops of NGF in the form of collyrium at a concentration of 250 μg/ml in balanced saline solution every two hours for 4 weeks. Treatment results were evaluated by objective exam, electroretinogram (ERG), blood flow from central retina artery (evaluated by OBF), contrast sensitivity, thickness of the layer of nervous fibers (evaluated by OCT), microperimetry and visus.

After 4 weeks of treatment all the considered parameters resulted remarkably better; particularly an improvement of ERG, blood flow, contrast sensitivity values and an increase of nervous fibers, microperimetry and visus were detected. Obtained data are summarised in the following Table 4.

ments carried out on animal models already disclosed in literature were repeated using, in addition to already disclosed intravitreous or retrobulbar administrations, also the administration of NGF in the form of collyrium, every two hours, at a concentration of 250 Ξg/ml in saline balanced solution. In all the experiments of crash and ischemic affection of optic nerve NGF administered in the form of collyrium exhibited the same activity as when administered using other administration routes.

On the base of results obtained from animals a total of 7 patients were treated, three of which suffering from low pressure glaucoma, two for retrobulbar neuritis and two for ischemic optic neuritis. Therapeutic protocol included the instillation of one-two drops of NGF in the form of collyrium at a concentration of 200 μg/ml in balanced saline solution every two hours for 4 weeks. Treatment results were evaluated by objective exam, visual evoked potentials (PEV), blood flow from central retina artery (evaluated by OBF), contrast sensitivity, thickness of the layer of nervous fibers (evaluated by OCT), microperimetry, visual field and visus.

After 4 weeks of treatment all the considered parameters resulted remarkably better; particularly an improvement of

TABLE 4

Effect of treatment with NGF in the form of collyrium on retina pathologies

| Pat. No. | Pathology | Age years Sex | Treatment form | Treatment with NGF | ERG[1] | OBF[2] | Contrast sensitivity | OCT[3] | Microperimetry | Visus |
|---|---|---|---|---|---|---|---|---|---|---|
| 1 | Pigmentary retinopathy | 35, F | collyrium | 4 weeks | ++ | + | ++ | + | + | ++ |
| 2 | Pigmentary retinopathy | 40, F | collyrium | 4 weeks | ++ | +/− | ++ | + | + | ++ |
| 3 | Pigmentary retinopathy | 32, M | collyrium | 4 weeks | +++ | ++ | ++ | + | ++ | ++++ |
| 4 | macular foramen | 55, F | collyrium | 4 weeks | + | + | + | +++ | +++ | +++ |
| 5 | senile macular degeneration | 70, F | collyrium | 4 weeks | + | +/− | + | ++ | +++ | +++ |
| 6 | senile macular degeneration | 73, M | collyrium | 4 weeks | +/− | +/− | + | ++ | ++ | + |
| 7 | miopic retinopathy | 26, M | collyrium | 4 weeks | + | + | + | ++ | +++ | +++ |

The values are expressed as improvement with reference to the values before the treatment with NGF:
"−" = constant or worsening;
"+/−" = improvement <10%;
"+" = improvement between 11% and 25%;
"++" = improvement between 26% and 50%;
"+++" = improvement between 51% and 75%;
"++++" = improvement higher than 75%;
[1]ERG = electroretinogram;
[2]OBF = blood flow of central retina artery;
[3]OCT = thickness of the nervous fiber layer.

Studies on the Effect of NGF in the Form of Collyrium for Optic Nerve Pathologies To evaluate the efficacy of the NGF administration on ocular surface in retina pathologies in a first step experi- PEV, blood flow, contrast sensitivity values and an increase of nervous fibers, microperimetry, visual field and visus were detected. The obtained data are summarised in the following Table 5.

TABLE 5

Effect of treatment with NGF in the form of collyrium on optic nerve pathologies

| Pat. No. | Pathology | Age years Sex | Treatment with NGF | PEV[1] | OBF[2] | Contrast sensitivity | OCT[3] | Micro-perimetry | Visual field | Visus |
|---|---|---|---|---|---|---|---|---|---|---|
| 1 | normal pressure glaucoma | 45, F | 4 weeks | +++ | ++ | ++ | ++ | ++ | ++ | ++ |
| 2 | normal pressure glaucoma | 37, F | 4 weeks | ++ | + | + | ++ | ++ | + | + |
| 3 | normal pressure glaucoma | 42, M | 4 weeks | + | ++ | + | ++ | ++ | ++ | ++ |
| 4 | idiophatic optic neuritis | 41, M | 4 weeks | ++ | ++ | + | + | ++ | + | ++ |
| 5 | idiophatic optic neuritis | 38, F | 4 weeks | ++ | ++ | + | +/− | + | +/− | + |
| 6 | ischemic optic neuritis | 52, F | 4 weeks | ++ | ++ | ++ | + | +/− | + | ++ |
| 7 | ischemic optic neuritis | 58, F | 4 weeks | ++ | ++ | + | ++ | ++ | + | ++ |

Values are expressed as improvement with reference to the values before the treatment with NGF:
"−" = constant or worsening;
"+/−" = improvement <19%;
"+" = improvement between 11% and 25%;
"++" = improvement between 26% and 50%;
"+++" = improvement between 51% and 75%;
"++++" = improvement higher than 75%;
[1] ERG = electroretinogram;
[2] OBF = blood flow of central retina artery;
[3] OCT = thickness of the nervous fiber layer.

Studies on the Effect of NGF for Vitreous Body Pathologies

A balanced saline solution containing 250 µg/ml of NGF was administrated three times a day for 4 weeks to 4 patients affected by myiodesopsia due to the presence of mobile vitreous bodies. After 4 weeks of treatment all the patients recognised symptomatology amelioration.

Studies on the effect of NGF for choroidea pathology

To evaluate the effect of external ophthalmic administration of NGF on choroidea pathologies an animal model of auotoimmune uveitis, obtained by administration of S retinal antigen to rats, was used. A group of animals every two hours was treated with one drop of NGF in the form of collyrium at a concentration of 200 µg/ml in saline balanced solution. After 4 weeks of treatment the lesions over vitreous body-retina in animals treated with NGF in the form of collyrium were compared to those present in animals treated with saline solution. In all the animals treated with NGF a reduction of tissues lesions was clearly visible.

The present invention was described with reference to specific embodiments thereof but it to be is intended that variations and modifications can be made by those skilled in the art without departing from the scope thereof.

The invention claimed is:

1. A method for treating glaucoma comprising: topically applying to an ocular surface of a human patient in need of such treatment an ophthalmic preparation comprising between about 10 µg/ml and about 500 µg/ml of nerve growth factor.

2. The method of claim 1, wherein the ophthalmic preparation comprises nerve growth factor in a pharmaceutically acceptable ophthalmic carrier and is in a form selected from the group consisting of solutions, suspensions, ointments, gels and liniments.

3. The method of claim 2, wherein the preparation is in the form of an ophthalmic solution.

4. The method of claim 2, wherein the nerve growth factor is of human origin.

5. The method of claim 4, wherein the nerve growth factor is a human recombinant nerve growth factor.

6. The method of claim 2 wherein the nerve growth factor is conjugated to a carrier molecule.

7. A method for treating optic neuritis comprising: topically applying to an ocular surface of a human patient in need of such treatment an ophthalmic preparation comprising between about 10 µg/ml and about 500 µg/ml of nerve growth factor.

8. The method of claim 7, wherein the preparation comprises nerve growth factor in a pharmaceutically acceptable ophthalmic carrier and is in a form selected from the group consisting of solutions, suspensions, ointments, gels and liniments.

9. The method of claim 8, wherein the preparation is in the form of an ophthalmic solution.

10. The method of claim 8, wherein the nerve growth factor is of human origin.

11. The method of claim 10 wherein the nerve growth factor is a human recombinant nerve growth factor.

12. The method of claim 8 wherein the nerve growth factor is conjugated to a carrier molecule.

13. The method of claim 1 wherein the preparation is buffered to pH 4-8.

14. The method of claim 7 wherein the preparation is buffered to pH 4-8.

* * * * *